United States Patent
Vogl et al.

(10) Patent No.: US 6,283,958 B1
(45) Date of Patent: *Sep. 4, 2001

(54) LASER APPLICATOR SET (75) Inventors: Thomas Vogl; Martin Mack, both of Berlin; Frank Kniep, Haberechtstrasse, all of (DE)

(73) Assignee: Somatex Medizintechnische Instrumente GmbH, Rietzneuendorf (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/155,958

(22) PCT Filed: Apr. 4, 1997

(86) PCT No.: PCT/DE97/00730

§ 371 Date: Dec. 3, 1998

§ 102(e) Date: Dec. 3, 1998

(87) PCT Pub. No.: WO97/37601

PCT Pub. Date: Oct. 16, 1997

(30) Foreign Application Priority Data

Apr. 4, 1996 (DE) ................................................ 196 14 780
Jan. 16, 1997 (DE) ................................................ 197 02 898

(51) Int. Cl.[7] .................................................. A61B 18/18
(52) U.S. Cl. .................................. 606/15; 606/10; 606/7; 606/20-23; 606/13; 606/14; 606/185; 607/89
(58) Field of Search .................................. 606/2, 3–7, 15, 606/185, 167; 128/6, 7, 303, 398

(56) References Cited

U.S. PATENT DOCUMENTS

| 4,681,104 | * | 7/1987 | Edelma | 128/303.1 |
| 4,693,244 | * | 9/1987 | Daikuzono | 128/303.1 |
| 4,854,315 | * | 8/1989 | Stack et al. | 128/303.1 |
| 4,959,063 | | 9/1990 | Kojima . | |
| 5,084,043 | * | 1/1992 | Hertzmann et al. | 606/3 |
| 5,169,396 | * | 12/1992 | Dowlatshahi et al. | 606/15 |
| 5,203,781 | * | 4/1993 | Bonati et al. | 606/15 |
| 5,246,436 | * | 9/1993 | Row | 606/13 |
| 5,250,068 | * | 10/1993 | Indeguchi et al. | 606/189 |
| 5,281,212 | * | 1/1994 | Savage et al. | 606/15 |
| 5,312,392 | | 5/1994 | Hofstetter et al. . | |
| 5,330,490 | | 7/1994 | Wilk et al. . | |
| 5,348,552 | * | 9/1994 | Nakajima et al. | 606/13 |
| 5,385,572 | * | 1/1995 | Nobles et al. | 606/185 |
| 5,507,742 | * | 4/1996 | Long et al. | 606/15 |

FOREIGN PATENT DOCUMENTS

| 4137983 | 6/1992 | (DE) . |
| 0634909 | 1/1995 | (EP) . |
| 673627 | 9/1999 | (EP) . |
| WO9203963 | 3/1992 | (WO) . |

* cited by examiner

Primary Examiner—Linda C. M. Dvorak
Assistant Examiner—Ahmed Farah
(74) Attorney, Agent, or Firm—Horst M. Kasper (57) ABSTRACT

A laser application set, which is an interventional application set for minimum invasive, laser-induced thermotherapy of soft-tissue tumors is disclosed.

The laser application set is designed in such a manner that an introductor tube (6) with a stylet (12) is provided and accommodates a tunneled catheter (17) with an internal stylet (20).

27 Claims, 5 Drawing Sheets

LASER APPLICATOR SET

The present invention discloses a laser application set, which is an interventional application set for minimum invasive laser-induced thermotherapy of soft-tissue tumors.

It is known as state of the art that laser radiation which emerges from an optical waveguide, e.g. the irradiation of an Nd:YAG laser at 1064 nm, employing a silica glass optical fiber (of the PCS, HCS or ALL SILICA type) as beam guidance system, may be used to cause radial-symmetric coagulation necroses in biological tissue. In order to do so, the light-conducting fiber is either placed upon the tissue or inserted into the tissue. However, the disadvantage of this method of therapy is that there occurs a high power density at the place of contact between fiber end area and tissue which, already above some 100 mW luminous power and depending on the fiber diameter, results in a carbonization of the tissue surface and thus, due to the high level of carbon absorption, prevents the further diffusion of radiation within the tissue.

Further an application device for laser radiation (DE4137983A1) is known, in which the beam-conducting end of the optical waveguide that faces the object to be treated is arranged in a tubular enveloping body whose front face is transparently shut to laser radiation, in particular in a plastic hose whose front end facing said object is air- and fluid-tight sealed, with the front face of the enveloping body and/or the end of the optical waveguide being equipped with a spreading device for laser radiation that has a spreading volume. There, also multiple chambered hoses are employed in order to provide possibly required cooling via a connected distributor piece.

Also known is a U.S. Pat. No. 5,312,392. A method of treating benign tumors". In which a trocar, that contains an optical waveguide, is inserted into the tumor to be treated. The position of the trocar with the optical waveguide is monitored using ultrasound. The disadvantage of this method is that any repositioning of the trocar with the optical waveguide is only possible with a new puncture.

The disadvantage of all previously applied methods of therapy is that they fail to allow for a repositioning of the relevant enveloping body which contains the laser and, hence, any faulty positioning of the laser or the enveloping body, respectively, requires a new puncture. A further disadvantage is that with a defective laser wire (optical waveguide) yet another intervention into the soft-tissue tumor to be treated becomes necessary.

The object of the invention is the implementation of a laser application set which ensures a gentle treatment of a patient and facilitates monitoring by means of a computer tomograph or a magnetic resonance tomograph, respectively.

The aim of the invention is the creation of a laser application set which neutralizes the disadvantages of the prior art and the previous methods of therapy by providing an interventional application set for laser therapy which enables a repositioning and requires only a single puncture of the tumor to be treated.

The aim according to the invention is attained by implementing a laser application set in accordance with Nos. 1 to 9 of the patent claims.

The laser application set consists of an introducer tube with an internal stylet. The internal stylet is locked with the introducer tube by means of a thread. The internal stylet is designed in such a manner that it projects by approx. 1 cm over and beyond the end of the introducer tube and has a pointed form. The stylet is of a hollow construction. A grip end at the external end of the stylet may be used to undo its locking by turning, after which the stylet may be removed from the introducer tube. The proximal end of the introducer tube is provided with a T piece. A silicone lamella is placed between the T piece and the introducer tube proper in order to provide a high elasticity during the insertion into the respective tumor. The silicone lamella is designed as a silicone membrane in the form of a forward-folding buckling lamella. A hose lead with a downstream three-way faucet is connected to the T piece. The hose lead and the connected three-way faucet may be used to apply cooling agents, lubricants and/or other additional local anesthetics. This opportunity of supply essentially contributes to providing a largely painless therapy also for capsular lesions. In addition, the hose lead allows for blood control of the patient under treatment during the therapy session. An external thread to lock the stylet is located opposite the silicone lamella of the T piece. Moreover, the T piece is equipped with a membrane which prevents any fluids from leaking during the therapy session.

A further preferred embodiment is the provision of the introducer tube with marks which facilitate the exact positioning of the application set. The individual marks are appended at a distance of 1 cm from each other.

A further component of the laser application set is a tunneled catheter with an internal stylet. The tunneled catheter with the internal stylet is inserted upon the removal of the stylet from the introducer tube. The tunneled catheter is designed in such a manner that its distal end is air- and fluid-tight sealed and has a tunneled catheter tip which significantly contributes to the possibility that a repositioning may be made of the tunneled catheter in the tumor to be treated. The tunneled catheter is also provided with marks at a distance of 1 cm from each other which allow for an exact positioning of the tunneled catheter when inserted into the introducer tube. The beginning of the marking on the tunneled catheter is designed in such a manner that, upon reaching the first mark, the catheter projects approx. 30 mm from out of the introducer tube, which is important for the operability of the laser application set. Within the tunneled catheter there is an internal stylet whose end is equipped with a grip end for its removal. The internal stylet is made from stainless steel, which preferentially consists of a paramagnetic material. This stainless steel wire is wrapped with a synthetic sheathing. The essential fact is that the internal stylet provides stabilization to the insertion of the tunneled catheter into the introducer tube and, hence, enables the exact positioning of the tunneled catheter tip into the tumor to be treated. A further essential feature of the invention is that the introducer tube with the stylet as well as the tunneled catheter with its internal stylet are made from materials which may be used for the monitoring of the method of therapy by means of computer tomography (CT) or magnetic resonance tomography (MRT), respectively. The materials of the introducer tube and the stylet as well as the tunneled catheter are preferably from synthetic materials, with PE, PTFE, FEP plastics being employed.

The laser application set according to the intervention has the following advantages over the known application sets for laser therapies of soft-tissue tumors.

The marks appended to the introducer tube allow for an exact positioning of the introducer tube on the patient. The exact position relation of the laser application set to the lesion is of decisive significance for a successful therapy. Further, it can be established that the membrane located in the T piece of the introducer tube facilitates a safe and non-slipping positioning of the tunneled catheter according to the invention. The tunneled catheter is thermoresistant up to a max. 400° C. and its distal end is air- and fluid-tight sealed. The tunneled catheter, which thus prevents a direct contact between the laser applicator and the patient, is equipped with an internal stylet, consisting of a wire from paramagnetic material, that essentially contributes to the stabilization of the tunneled catheter during its insertion. Thus, on the one hand the tunneled catheter may be kept thin while, on the other, the required stabilization is still achieved. The marks appended to the introducer tube allow for an exact positioning of the introducer tube and prevent a fusion of the introducer tube when the light transmitting tunneled catheter fails to project sufficiently from the introducer tube system that is impervious to laser light. A repositioning of the tunneled catheter, which is inserted internally into the introducer tube, is permitted as a result of permanent monitoring by computer tomograph or a magnetic resonance tomograph, respectively. In case that a defect or other malfunction is found during the insertion of the laser applicator a new laser applicator may be inserted at any time without having to commence a new therapy phase. The appropriate composition of materials has created a laser application set which is compatible with monitoring by CT, MRT or nuclear magnetic resonance tomography (NMRT), respectively.

A further advantage according to the invention lies in that upon the completion of the laser therapy and removal of the introducer tube therapeutic agents, such as tissue glue, may be introduced via the hose lead and the pertaining three-way faucet, and thus a dispersion of the cells of the treated tumor is inhibited which previously had been a serious disadvantage in the laser therapy of tumors.

Furthermore, the laser application set according to the invention facilitates the single-time puncture of the tumor to be treated, thus preventing any dispersion of the tumor.

The following aspects should be considered as further application indications of the laser application set according to the invention. The laser application set according to the invention enables a percutaneous laser therapy of, e.g., hepatic metastases which cannot be surgically removed due to their distribution. Also operable metastases may be subjected to laser therapy when a patient refuses surgery. In addition, a patient may be brought into an operable condition by employing the laser application set to treat one or more metastases by laser treatment. The set allows for the treatment of metastases of a max. diameter of 4 cm. Further fields of application of the laser application set worth mentioning are the palliative therapy of benign tumors in the head/neck region and the percutaneous therapy of soft-tissue tumors in the pelvic region.

The tunneled catheter is designed with a connection piece. The locking piece of an inner tunneled catheter is appended to the connection piece, with the inner tunneled catheter being located within the tunneled catheter of the laser application set. A flushing and/or cooling agent outlet is provided at the distal end of the inner tunneled catheter The connection piece of the tunneled catheter and the locking piece of the inner tunneled catheter may be firmly interlocked by means of a sealing thread at the connection piece. The connection piece and the locking piece are each equipped with connectors to which T pieces are attached. The T pieces may be used to connect a pump for the recirculation of the flushing and/or cooling agent. Thus, a flushing and/or cooling fluid, preferably sterile isotonic sodium chloride solution, is led via a T piece of the inner tunneled catheter and on via the connector of the locking piece into the inner tunneled catheter, with the backflow occurring between the inner tunneled catheter and tunneled catheter via the connection piece and the connector to the T piece. Thus optimum cooling is provided to the entire area of the punctured external tissue.

The locking piece of the inner tunneled catheter is equipped with a membrane sealing. The internal stylet of the laser application set is inserted and removed, respectively, and also the laser applicator is inserted during a therapy session through this membrane sealing. A further membrane sealing at the connection piece serves as a sealing when the inner tunneled catheter is inserted into the tunneled catheter.

The particular design of the tunneled catheter provides further essential advantages for the use of the laser application set. The employment of the laser application set ensures optimum conditions to achieve coagulation necroses with a max. diameter of 20 mm to 25 mm. It is due to the heat dissipation, that is essentially conditioned by blood flow in the vessels and diffusion in the tissue, that it is usually impossible in vivo to induce coagulation necroses larger than 2*2*2 cm by using the laser application set without inserting the inner tunneled catheter. However, the majority of soft-tissue tumors have a size of 3 cm to 4 cm when a diagnosis is made. In order to coagulate a volume of 4*4*4 cm, with the previous use of the laser application set of the main patent, eight laser applications and, hence, eight punctures are necessary. The laser power is approx. 5 watts applied over a 20-minute therapy session.

What is essential is that the tunneled catheter configuration allows the laser application set to achieve coagulation necroses larger of up to a max. 4.2*4.2*4.2 cm with one laser application, during which laser power of up to 30 watts is applied up to 15 minutes. The tunneled catheter, which is used as part of the laser application set, achieves that high laser powers can only be applied when a cooling of the tissue immediately adjacent to the tunneled catheter is ensured and thus any carbonization or vaporization of tissue is prevented. Carbonization or vaporization of the tissue immediately adjacent to the tunneled catheter prevents a further propagation of the coagulation zone since the entire laser power at the employed wavelength of 1064 nm would be absorbed in the immediate vicinity of the tunneled catheter. In particular the laser application catheter in conjunction with the tunneled catheter of the laser application set in the main application yields the below advantages for the patient:

1. In order to coagulate a lesion measured to be 4*4*4 cm the use of a tunneled catheter in conjunction with the laser application set requires only one laser application in the place of eight laser applications with the laser application set.
2. Furthermore, the clear decrease of the number of punctures reduces the risk of puncture complications, such as hemorrhage, vascular and nerve injuries as well as organ injuries.
3. Since the number of punctures required for tumor treatment decreases also the risk of tumor dispersion and thus the risk of vaccination metastasis is reduced.
4. Furthermore, the use of the special tunneled catheter in conjunction with the laser application set results in a clear cost saving potential of this method because with a lesion measured to be 4*4*4 cm no longer eight puncture tracks have to be sealed wit fibrin glue but only one puncture track.
5. Normally, a patient does not tolerate eight punctures in one therapy session, hence, the second half of the tumor often had to be subject to laser therapy in a second therapy session. This second therapy session may fall away when the tunneled catheter of the laser application set is used.

6. In case of lesions up to a diameter of 4 cm the use of the tunneled catheter with the laser application set attains a clearly higher probability of a 100% tumor coagulation. Thus, this application is able to achieve a clear reduction of the local recurrence rate.

The advantageous further developments of the invention are, respectively, characterized in the dependent claims or are represented below in greater detail together with a description of the preferred practical example of the invention by means of figures. The figures illustrate the following:

Figure 1:
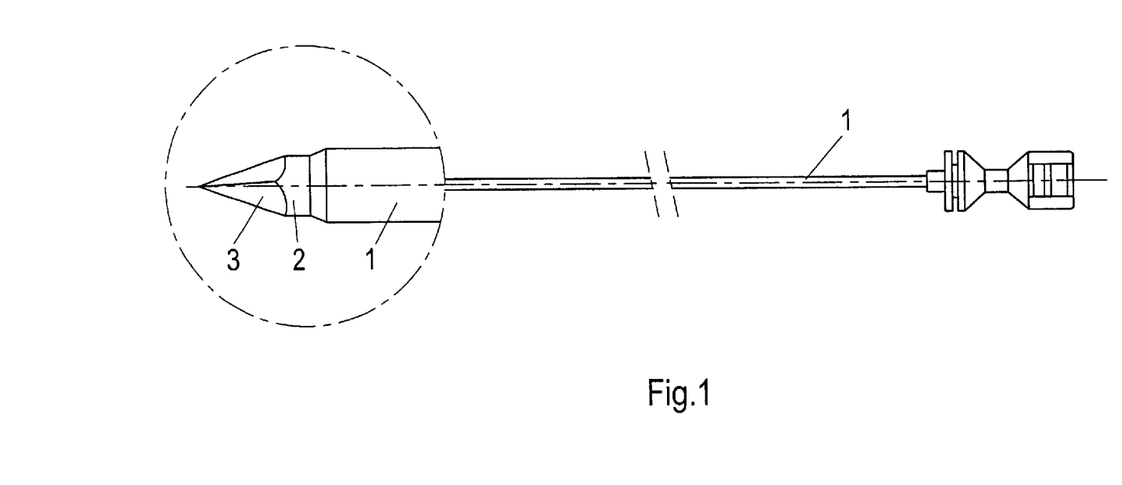
FIG. 1 Puncture needle
FIG. 2 Stainless steel wire.

FIG. 1 illustrates a puncture needle 1 with a contained needle stylet 2, which has a needle stylet tip 3. The puncture needle is of a known design. What is essential is that the puncture needle 1 consists of a paramagnetic material and thus may be applied in the MRT process. The puncture needle 1 has a length of approx. 200 mm and a diameter of approx. 1.3 mm. The needle stylet has a three-edged puncture tip which extends beyond the puncture needle 1. A grip end enables the smooth removal of the needle stylet 2 from the puncture needle 1.

Figure 2:
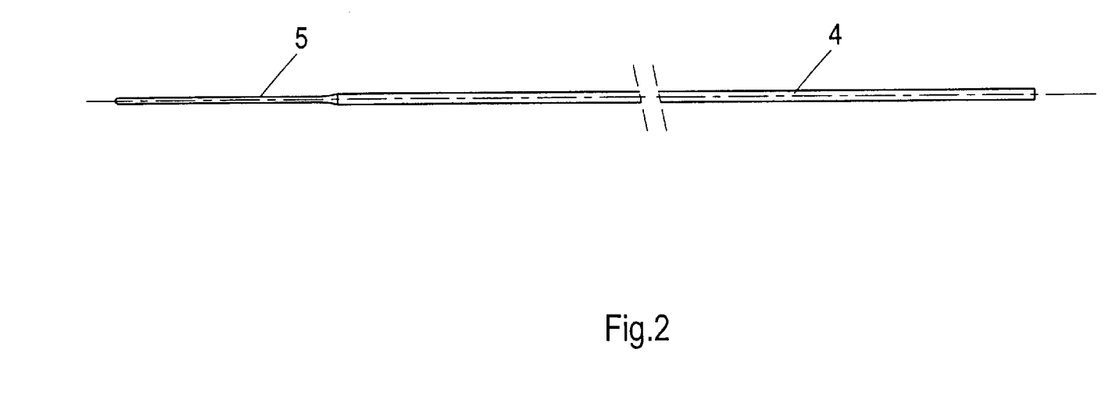

FIG. 2 illustrates a wire 4, which consists of stainless steel, with a special type of this wire 4 with a tongue end 5 being available, which is executed with a taper-ground tongue. In the depicted practical example the length of the wire is approx. 1 meter, with the tongue end 5 being approx. 100 mm long. The wire 4 is made from a paramagnetic material.

Figure 3:
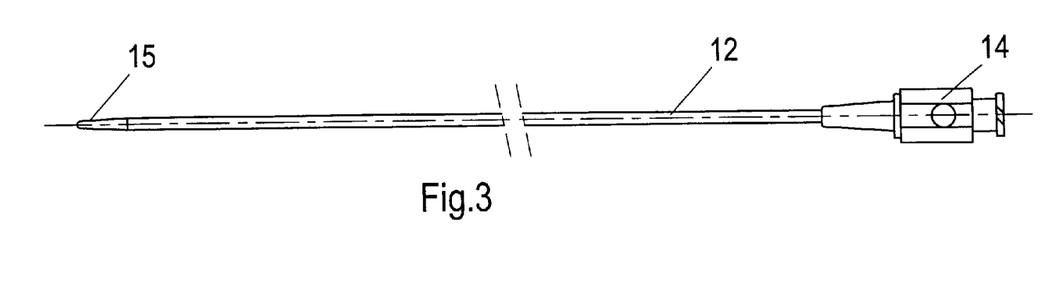
FIG. 3 Stylet introducer tube.
Figure 4:
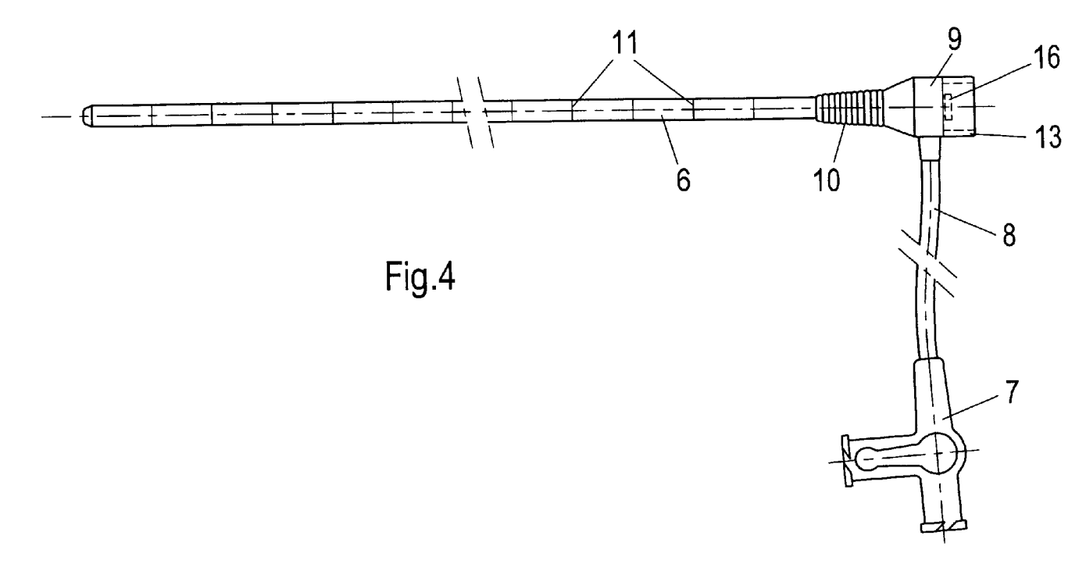
FIG. 4 Introducer tube with T piece.

FIGS. 3 and 4 illustrate the introducer tube 6 and the stylet 12. The introducer tube 6 and the stylet 12 are made from synthetic materials, such as PE, PTFE, FEP. The length of the introducer tube 6 is approx. 100–200 mm and its diameter is approx. 1.5 mm up to 4 mm—depending on the practical example. The stylet 12 that is contained in the introducer tube 6 is executed with close tolerances—depending on the size of the introducer tube 6. The proximal end of the introducer tube 6 is equipped with a silicone lamella 10 to which a T piece 9 is connected. This silicone lamella 10 is designed as a silicone membrane in the form of a forward-folding buckling lamella. The silicone lamella 10 essentially improves handling of the introducer tube 6. The T piece 9 is equipped with a hose lead 8 and an adjacent three-way faucet 7. Via the three-way faucet 7 and the hose lead 8 to the T piece 9 it is possible to apply additional local anesthetics, such as lubricant, tissue glue, alcohol, etc., which essentially contributes to providing a largely painless therapy also for capsular lesions. Furthermore the T piece 9 is equipped with an external thread 13 to lock the stylet 12 with contained internal thread into the grip end 14. A membrane 16 is provided between the T piece 9 and the adjacent external thread 13 which prevents any fluids from leaking and facilitates a safe and non-slipping positioning of the tunneled catheter 17. The introducer tube 6 is provided with marks 11. These are preferably arranged at a distance of 1 cm from each other along the entire length of the introducer tube 6. Thus an exact positioning of the introducer tube 6 is ensured. In its locked state with the introducer tube 6 the stylet 12 has a length which is distinguished in that approx. 1 cm of the stylet tip 15 extend from the distal end of the introducer tube 6.

A further preferred design is that the stylet 12 is executed hollow. This hollow design form of the stylet 12 provides an increased lubricity during the insertion of the introducer tube 6 with the stylet 12 via the wire 4 into the patient.

Figure 5:
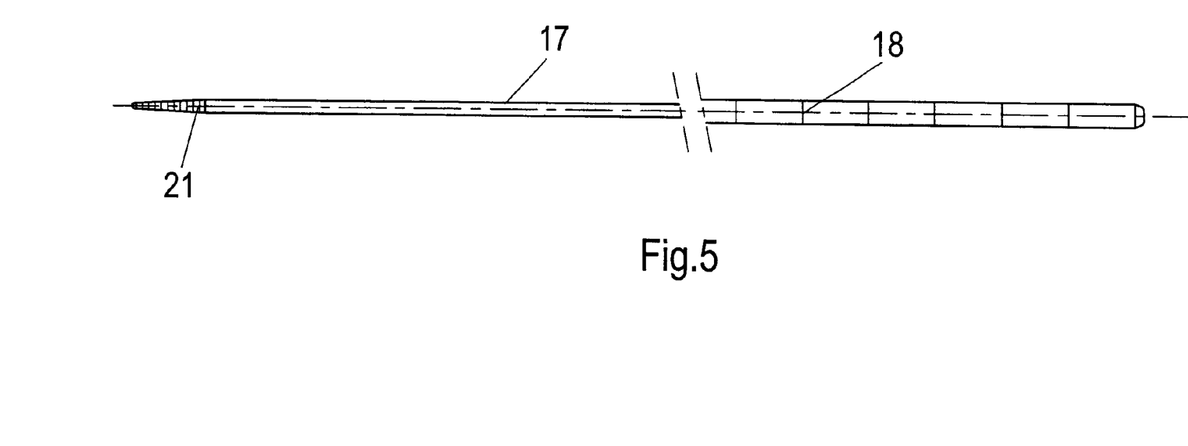
FIG. 5 Tunneled catheter.
Figure 6:
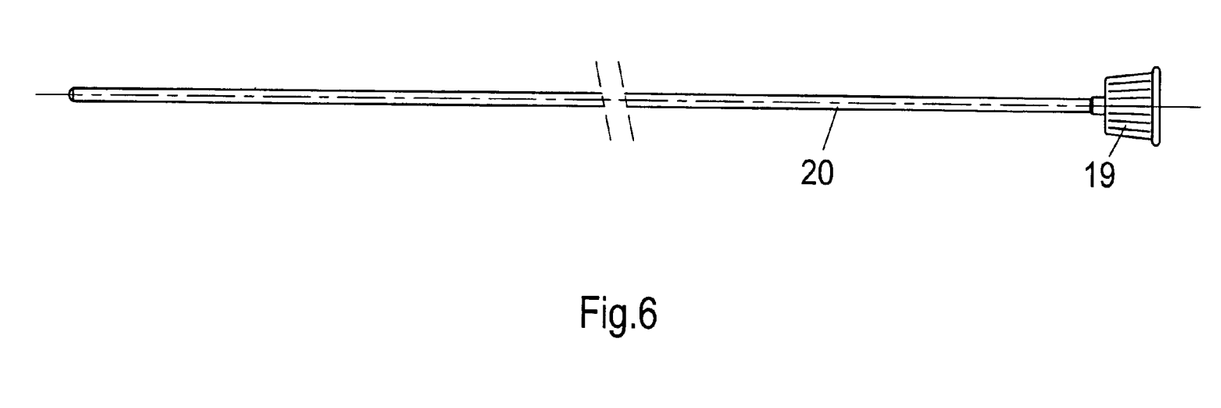
FIG. 6 Internal stylet—tunneled catheter.

FIGS. 5 and 6 illustrate the tunneled catheters 17 according to the invention with internal stylet 20. The tunneled catheter 17 made from a thermostable synthetic material which resists a max. temperature of 400° C. The preferred materials employed are PTFE and FEP. The tunneled catheter 17 has a length of approx. 400 mm. Essential of the invention is here the existing tip at the distal end of the tunneled catheter which is air- and fluid-tight sealed. The external diameter of the tunneled catheter may be between 1.5 mm and 4 mm, depending on the application form. This tunneled catheter 17 is equipped with an internal stylet 20 with a grip end 19. The internal stylet 20 is a wire which is made from a paramagnetic material and provided with a plastics coating. It is through this internal stylet 20 that the tunneled catheter 17, due to the high stability of the stainless steel wire, may be inserted with safe placing in the internal stylet 20, and there are further control opportunities for the positioning of the tunneled catheter 17. The upper part of the tunneled catheter 17 is provided opposite the tunneled catheter tip 21 with marks which are arranged at a distance of 1 cm from each other. The first mark towards the tunneled catheter tip 21 is arranged in such a manner that approx. 30 mm of the tunneled catheter 17 project at the distal end of the introducer tube 6 upon insertion into the introducer tube 6 and reaching of the first mark. After removing the internal stylet 20 by the grip end 19 an optical waveguide for laser treatment of the respective tumor may be smoothly inserted. The positioning of the tunneled catheter 17 towards the introducer tube 6 by means of the marks on the tunneled catheter 17 according to the invention largely prevents that a fusion of the light source with the light impervious introducer tube 6 occurs during treatment with the optical waveguide since the tunneled catheter 17 always projects approx. 30 mm from the distal end of the introducer tube 6.

Figure 7:
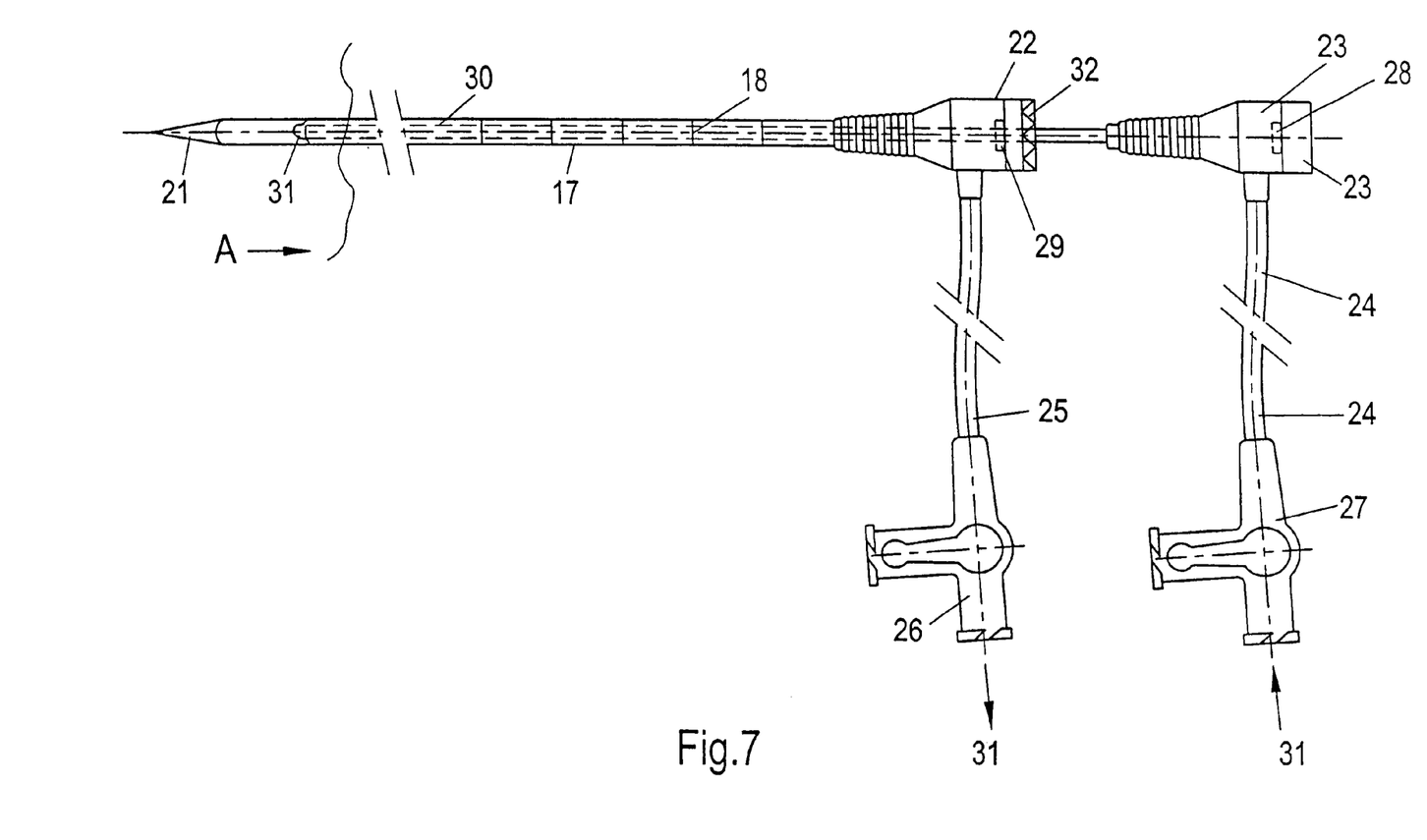
FIG. 7 Tunneled catheter with cooler.

FIG. 7 illustrates a special embodiment of the tunneled catheter with cooling which is made up as follows. The tunneled catheter 17 of the laser application set is employed in the same manner, with the proximal end of the tunneled catheter 17 being equipped with a connection piece 22. A T piece 26 is connected to the connection piece 22 via a connector 25. A pump to convey flushing and/or cooling agent is attached to the T piece 26. A sealing thread at the connection piece 22 firmly interlocks a locking piece 23 of the inner tunneled catheter 30. The inner tunneled catheter 30 is located inside the tunneled catheter 17. The inner tunneled catheter 30 is designed in such a manner that it ends at the distal end 5 mm before the tunneled catheter tip 21. The inner tunneled catheter 30 is open at the distal end. A connection of a pump for a flushing and/or cooling agent is provided via a connector 24 and a T piece 27 above the locking piece 23 of the inner tunneled catheter 30. The cooling agent 31 flows via the T piece 24, connector 25, locking piece 23 and through the inner tunneled catheter 30 into the tip of the of the inner tunneled catheter 30 and on its flow back the flushing and/or cooling agent 31 is led between the tunneled catheter 17 and the inner tunneled catheter 30 via the connection piece 22, connector 25 and T piece 26 to the pump. Preferably a sterile isotonic sodium chloride solution is used as flushing and/or cooling agent. The laser applicator 33 is inserted into the inner tunneled catheter 30, thus ensuring maximum cooling of the entire punctured tissue, since the backflow between the tunneled catheter 17 and the inner tunneled catheter 30 transmits cooling to the entire area of the punctured tissue—which consists an advantage that is essential of the invention. In order to seal off the of the laser applicator 33 or the removal of the internal stylet 20 of the laser application set, respectively, a membrane sealing 28 is arranged in the locking piece 23 of the inner tunneled catheter 30. In order to seal off the insertion of the inner tunneled catheter 30 a further membrane sealing 29 is provided in the connection piece 22.

Figure 8:
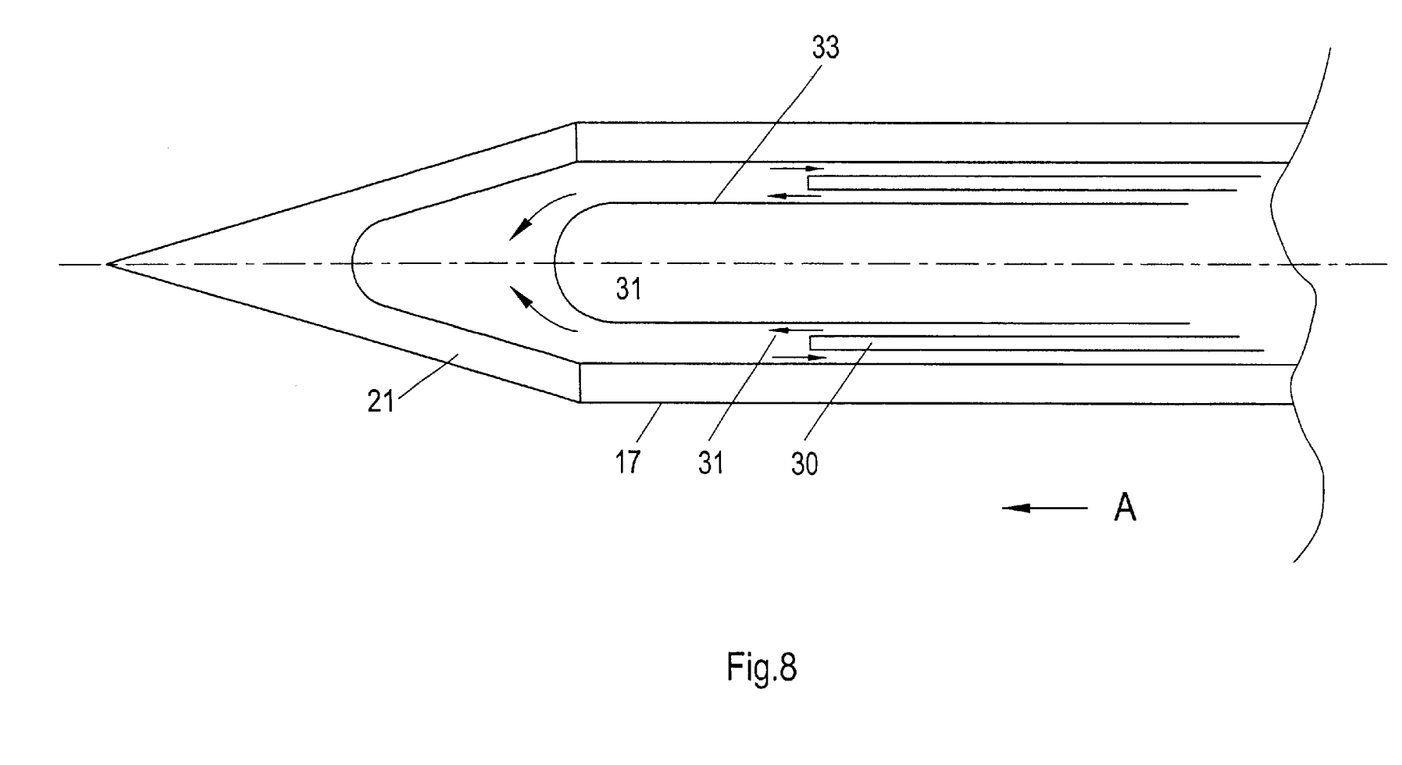
FIG. 8 Tip of the tunneled catheter with cooler.

FIG. 8 illustrates the tip of the tunneled catheter 17 in its embodiment. It can be seen that the cooling agent 31 exits in the interior of the inner tunneled catheter 30 and at the outside of the tunneled catheter point 21 between the inner tunneled catheter 30 and the tunneled catheter 17. The laser applicator 33 projects beyond the distal end of the inner tunneled catheter 30, hence, the flushing and/or cooling agent cools the entire external tissue of the tumor to be treated.

The application according to the invention of the laser application set in a therapy of soft-tissue tumors is described as follows:

The tumor to be treated is punctured with the puncture needle 1 and the contained needle stylet 2 with its needle stylet tip 3. The three-edged needle stylet tip 3 makes for a good puncture efficiency of the puncture needle 1. Following the completion of a positive puncture the needle stylet 2 is removed from the puncture needle 1. Subsequently, a wire 4 is inserted up to the distal end of the puncture needle 1. The puncture needle 1 is removed via this wire 4. Then the introducer tube 6 with the locked stylet 12 is strung to the wire 4 and led into the tumor to be treated up to the distal end of the wire 4. The wire 4 is removed after the exact positioning of the introducer tube 6 with the stylet 12. As required, the necessary additional local anesthetics are supplied to the three-way faucet 7. A slight turn of the grip end 14 of the stylet 12 undoes the locking with the T piece 9 of the introducer tube 6 and the stylet 12 may be removed from the introducer tube 6.

A further preferred design is that marks are appended to the introducer tube 6 which permit an exact positioning of the introducer tube 6 into the tumor to be treated. Subsequently, the tunneled catheter 17 with contained internal stylet 20 is inserted into the introducer tube 6. While doing so, the marks on the tunneled catheter 17 permit an exact positioning of the introducer tube 6 into the tumor to be treated, with, as is essential of the invention, the first mark being designed in such a way that the tunneled catheter 17 projects by 30 mm from the distal end of the introducer tube 6. The internal stylet 20 is provided to improve correctability and stabilization during the insertion of the tunneled catheter 17. Following the removal of the internal stylet 20 by means of the grip end 19 an optical waveguide to perform the laser therapy is inserted until the distal end of the tunneled catheter 17. The permanent monitoring by means of CT or MRT processes, respectively, permits a respective exact positioning of the tunneled catheter 17 with the tunneled catheter point 21 according to the invention. Furthermore, the functioning of the inserted optical waveguide can be checked in order to prevent a fusion of the light source with the light impervious sheath of the introducer tube 6. The exact positioning with the help of the introducer tube 6 and the tunneled catheter 17 also enables the removal of defective optical waveguides and to replace such by a new optical waveguide and thus avoid a new puncture. Following the completion of the treatment via optical waveguide the latter is removed and subsequently also the tunneled catheter 17 and the introducer tube 6. While doing so it possible to introduce, e.g., tissue glue via the three-way faucet 7 and the hose lead 8 to the T piece 9 during the removal of the introducer tube 6 and thus an advantage according to the invention is provided by ensuring a minimum cell dispersion of the treated tumor while removing the introducer tube 6 which previously has been an essential disadvantage of the laser therapy of tumors.

REFERENCE SIGNS

1. Puncture needle
2. Needle stylet
3. Needle stylet tip
4. Wire
5. Tongue-shaped end
6. Introductor tube
7. Three-way faucet
8. Hose lead
9. T piece
10. Silicone lamella
11. Mark
12. Stylet
13. External thread
14. Grip end
15. Stylet tip
16. Membrane
17. Tunneled catheter
18. Mark
19. Grip end
20. Internal stylet
21. Tunneled catheter tip
22. Connection piece
23. Locking piece
24. Connection
25. Connection
26. T piece
27. T piece
28. Membrane sealing
29. Membrane sealing
30. Inner tunneled catheter
31. Flushing and/or cooling fluid
32. Sealing thread
33. Laser applicator

What is claimed is:

1. A laser application set to treat tumors comprising a tunneled catheter (17) having a distal end and made of synthetic materials, preferably PE, FEP, PTFE, wherein the distal end of the tunneled catheter (17) is air- and fluid-tightly sealed and movably guides an optical waveguide (33), a puncturing needle (1) for performing initial penetration and for introducing of an introducer tube (6), wherein the introducer tube (6) is furnished with a closely fitting interior stylet (12) and wherein the tunneled catheter (17) is fitted with a closely fitting internal stylet (20), in which, upon removal of the stylet (12) from the introducer tube (6), the tunneled catheter (17) with the internal stylet (20) is close-fittingly inserted into the introducer tube (6) and projects from the distal end of the introducer tube (6) and in which an optical waveguide (33) is inserted after removal of the internal stylet (20) from the tunneled catheter (17).

2. The laser application set according to claim 1, wherein the introducer tube (6) and the interior stylet (12) are open at their distal and proximal ends.

3. The laser application set according to claim 2, wherein the proximal end of the introducer tube (6) is equipped with a T piece (9), with a silicone lamella (10) being placed between the T piece (9) and the introducer tube (6) and an external thread (13) fitted to the opposite side, with an interior membrane (16) and a hose lead (8) at the T piece (9) with a three-way faucet (7) fitted to its end.

4. The laser application set according to claim 3, wherein the stylet (12) is equipped with a grip end (14) with an internal thread which, in conjunction with the external thread (13) of the introducer tube (6), enables to lock the stylet (12).

5. The laser application set according to claim 2, wherein the introducer tube (6) and the stylet (12) are hollow and made from a material which is suitable for MRT processes.

6. The laser application set according to claim 5, wherein the introducer tube (6) and the stylet (12) are made of a member of the group selected from polyethylene plastics (PE-plastics), polytetrafluoroethylene plastics (PTFE-plastics), copolymerizates of tetrafluoroethylene and hexafluoropropylene plastics (FEP-plastics) and mixtures thereof.

7. The laser application set according to claim 1, wherein the distal end of the tunneled catheter (17) is fitted with a tunneled catheter tip (21) and has an opening at its proximal end.

8. The laser application set according to claim 1, wherein the introducer tube (6) and the tunneled catheter (17) are each provided with marks (18) and (11) so that the tunneled catheter (17) projects 30 mm beyond a distal end of the introducer tube (6) upon introduction into the introducer tube (6).

9. The laser application set according to claim 8, wherein the marks (11, 18) are arranged at a distance of 1 cm from each other, with the introducer tube (6) being marked along its entire length.

10. The laser application set according to claim 2, wherein the introducer tube (6) and the stylet (12) are hollow and made from a material which is suitable for MRT processes, preferably PE, FEP, PTFE.

11. The laser application set according to claim 1, wherein the internal stylet (20) is made of a wire, which preferably is from a paramagnetic material, and is enclosed by a synthetic sheathing.

12. The laser application set according to claim 1, wherein the tunneled catheter (17) has an inner tunneled catheter (30), and a firm connection between the two catheters (17 and 30) can be made, and a space exists between the tunneled catheter (17) and the inner tunneled catheter (30), in which a laser applicator (33) is movably arranged.

13. The laser application set according to claim 1, wherein, in order to establish a firm, separable connection, a connection piece (22) is arranged at the tunneled catheter (17) and a locking piece (23) at the inner tunneled catheter (30), in which the connection piece (22) is provided with a sealing thread (32).

14. The laser application set according to claim 13, wherein the locking piece (23) is provided with a membrane sealing (28) which is connected to a T piece (27) by means of a connector (24).

15. The laser application set according to claim 14, wherein a pump to convey a flushing and/or cooling agent (31) is connected to the T piece (27).

16. The laser application set according to claim 14, wherein a pump to convey a flushing or cooling agent (31) is connected to the T piece (26).

17. The laser application set according to claim 15, wherein a pump to convey a flushing or cooling agent (31) is connected to the T piece (27).

18. The laser application set according to claim 13, wherein a flushing or cooling agent (31), which is conveyed via the inner tunneled catheter (30) into the tunneled catheter (17) is preferably sterile isotonic sodium chloride solution.

19. The laser application set according to claim 13, wherein the inner tunneled catheter (30) ends 5 mm before a tunneled catheter tip (21) at the distal end.

20. The laser application set according to claim 13, characterized in that the inner tunneled catheter (30) is designed in such a manner that a backflow of flushing and/or cooling agent is ensured between the tunneled catheter (17) and the inner tunneled catheter (30).

21. A laser application set for the treatment of tumors consisting of a puncturing needle (1) for performing initial penetration, an introducer tube (6) with an interior stylet (12) to be introduced by the puncturing needle (1) as well as a tunneled catheter (17) with an inner tunneled catheter (30), in which a movable optical waveguide (33) is positioned within the inner tunneled catheter (30), characterize in that a tunneled catheter (17) is designed in such a way, that the tunneled catheter (17) is provided with an internal stylet (20) which, without the addition of a flushing or cooling agent (31) for the optical waveguide (33), is inserted into the introducer tube (6); the optical waveguide (33) is positioned in the tunneled catheter (17) after removal of the internal stylet (20), that an inner tunneled catheter (30) is positioned in the tunneled catheter (17) with the addition of a flushing or cooling agent (31) for the optical waveguide (33) and is inserted into the introducer tube (6), the proximal end of the introducer tube (6) is equipped with a device used respectively for the application of liquids into the stitch track towards the tumors or blood testing during an ongoing therapy.

22. The laser application according to claim 21, characterized in that the device for the application of liquids or blood testing at the proximal end of the introducer tube (6) is equipped with a T piece (9), with a silicone lamella (10) being placed between the T piece (9) and the introducer tube (6) and an external thread (13) being fitted to the opposite side, with an interior membrane (16) and a hose lead (8) at the T piece (9) with a three-way faucet (7) fitted to its end.

23. A laser application set for the treatment of tumors comprising a puncturing needle for preforming initial penetration;

an insertion tube to be introduced by the puncturing needle and having a proximal end, wherein the proximal end of the insertion tube is equipped with a device used respectively for the application of liquids into the stitch track towards the tumor or blood testing during an ongoing therapy;

an interior stylet disposed at the introducer tube;

a tunneled catheter having a distal end disposed at the introducer tube, wherein the distal end of the tunneled catheter is sealed and wherein the tunneled catheter is finished with the internal stylet;

an inner tunneled catheter disposed in the tunneled catheter and introduced in the insertion tube;

a moveable optical waveguide disposed within the inner tunneled catheter, wherein the internal stylet is inserted into the insertion tube without an addition of a flushing agent or cooling agent for the optical waveguide, and wherein the optical waveguide is positioned in the inner tunneled catheter after removal of the internal stylet from the tunneled catheter, and wherein the inner tunneled catheter furnishes an addition of flushing or cooling agent to the optical waveguide and is inserted into the insertion tube.

24. A laser application set to treat tumors comprising a puncturing needle for performing initial penetration;

a tunneled catheter having a distal end and made of synthetic materials, wherein the distal end of the tunneled catheter is air- and fluid-tightly sealed;

an optical waveguide, wherein the distal end of the tunneled catheter movably guides the optical waveguide;

an introducer tube to be introduced by the puncturing needle;

a closely fitting interior stylet furnished at the introducer tube, wherein the tunneled catheter is fitted with the closely fitting internal stylet, wherein, the tunneled catheter with the internal stylet is close-fittingly inserted into the introducer tube upon removal of the stylet from the introducer tube and wherein the internal stylet projects from the distal end of the tunneled catheter and wherein the optical waveguide is inserted after removal of the internal stylet from the tunneled catheter.

25. The laser application set according to claim 24, wherein the introducer tube and the stylet are made of a member of the group selected from polyethylene plastic (PE-plastics), polytetrafluoroethylene plastics (PTFE-plastics), copolymerizates of tetrafluoroethylene and hexafluoropropylene plastics (FEP-plastics) and mixtures thereof.

26. A laser application set for the treatment of tumors comprising a puncturing needle for performing initial penetration;

an insertion tube to be introduced by the puncturing needle and having a proximal end, wherein the proximal end of the insertion tube is equipped with a device used respectively for the application of liquids into the stitch track towards the tumor or blood testing during an ongoing therapy;

an interior stylet disposed at the introducer tube;

a tunneled catheter having a distal end, disposed at the introducer tube and wherein the tunneled catheter is furnished with an internal stylet and wherein the distal end of the tunneled catheter is sealed an inner tunneled catheter disposed in the tunneled catheter and introduced in the insertion tube;

a movable optical waveguide disposed within the inner tunneled catheter, wherein the internal stylet is inserted into the insertion tube without an addition of a flushing agent or cooling agent for the optical waveguide, and wherein the optical waveguide is positioned in the inner tunneled catheter after removal of the internal stylet from the tunneled catheter, and wherein the inner tunneled catheter furnishes an addition of a flushing or cooling agent to the optical waveguide and is inserted into the insertion tube.

27. The laser application set to treat tumors according to claim 26, wherein the optical waveguide projects beyond the distal end of the inner tunneled catheter, and wherein the cooling agent is led between the optical waveguide and the inner tunneled catheter toward a tip of the tunneled catheter and wherein the cooling agent is led between the inner tunneled catheter and the tunneled catheter away from the tip of the tunneled catheter such that the cooling agent cools an entire external tissue of a tumor to be treated.

* * * * *